US010966889B2

(12) United States Patent
Ribble et al.

(10) Patent No.: US 10,966,889 B2
(45) Date of Patent: Apr. 6, 2021

(54) SUPPORT APPARATUSES COMPRISING COOLING ELEMENTS

(71) Applicant: Hill-Rom Services, Inc., Batesville, IN (US)

(72) Inventors: David Lance Ribble, Batesville, IN (US); Varad Narayan Srivastava, Batesville, IN (US); David Lawrence Bedel, Batesville, IN (US)

(73) Assignee: HILL-ROM SERVICES, INC., Batesville, IN (US)

( * ) Notice: Subject to any disclaimer, the term of this patent is extended or adjusted under 35 U.S.C. 154(b) by 240 days.

(21) Appl. No.: 15/840,127

(22) Filed: Dec. 13, 2017

(65) Prior Publication Data

US 2018/0185224 A1 Jul. 5, 2018

Related U.S. Application Data

(60) Provisional application No. 62/439,933, filed on Dec. 29, 2016.

(51) Int. Cl.
*A61G 7/057* (2006.01)
*A61F 7/00* (2006.01)
(Continued)

(52) U.S. Cl.
CPC ........ *A61G 7/05746* (2013.01); *A61F 7/0053* (2013.01); *A61G 7/057* (2013.01);
(Continued)

(58) Field of Classification Search
USPC .............................................. 607/114; 5/423
See application file for complete search history.

(56) References Cited

U.S. PATENT DOCUMENTS 4,949,412 A * 8/1990 Goode ............... A61G 7/05769
5/713
5,325,551 A * 7/1994 Tappel ................. A47C 27/082
5/709

(Continued)

FOREIGN PATENT DOCUMENTS

WO      2005007054 A1    1/2005
WO   WO-2017016973     *  2/2017

OTHER PUBLICATIONS

Extended European Search Report for EP19187945 dated Sep. 30, 2019.

*Primary Examiner* — Joseph A Stoklosa
*Assistant Examiner* — Adam J Avigan
(74) *Attorney, Agent, or Firm* — Dinsmore & Shohl LLP (57) ABSTRACT

A support apparatus configured to support a person is provided. The support apparatus includes a top surface including one or more predetermined areas, one or more conduits located inside the support apparatus which are located proximate to the one or more predetermined areas, and an air supply configured to provide air to the one or more conduits for delivering to the one or more predetermined areas. The air supply includes a temperature sensor configured to measure a temperature of the air provided by the air supply, a cooling element, and a controller communicatively coupled to the temperature sensor and the cooling element. The controller determines whether the measured temperature of the air is higher than a predetermined temperature, and controls the cooling element to cool the air to the predetermined temperature if it is determined that the temperature of the air is higher than the predetermined temperature.

18 Claims, 8 Drawing Sheets

(51) Int. Cl.
  *A47C 21/04* (2006.01)
  *A61B 6/04* (2006.01)
  *A61G 13/12* (2006.01)
(52) U.S. Cl.
  CPC ............... *A47C 21/04* (2013.01); *A61B 6/045* (2013.01); *A61F 7/0085* (2013.01); *A61F 2007/0027* (2013.01); *A61F 2007/0045* (2013.01); *A61F 2007/0055* (2013.01); *A61F 2007/0057* (2013.01); *A61F 2007/0096* (2013.01); *A61G 7/05784* (2016.11); *A61G 13/1275* (2013.01); *A61G 2203/20* (2013.01); *A61G 2203/46* (2013.01); *A61G 2205/20* (2013.01); *A61G 2210/70* (2013.01)

(56) References Cited

U.S. PATENT DOCUMENTS

| | | | | |
|---|---|---|---|---|
| 5,699,570 A | * | 12/1997 | Wilkinson | A47C 27/082 5/713 |
| 5,728,147 A | * | 3/1998 | Thomas | A61F 7/00 5/655.9 |
| 5,800,480 A | * | 9/1998 | Augustine | A61F 7/10 607/96 |
| 5,837,002 A | * | 11/1998 | Augustine | A47C 21/044 607/104 |
| 5,891,187 A | * | 4/1999 | Winthrop | A61F 7/00 126/204 |
| 6,073,291 A | * | 6/2000 | Davis | A61B 6/0485 414/676 |
| 6,517,510 B1 | * | 2/2003 | Stewart | A61F 7/02 417/207 |
| 6,606,754 B1 | * | 8/2003 | Flick | A47C 21/044 5/421 |
| 6,701,544 B2 | | 3/2004 | Heimbrock | |
| 6,855,158 B2 | * | 2/2005 | Stolpmann | A61F 7/00 5/421 |
| 6,855,185 B2 | | 2/2005 | Osako et al. | |
| 7,278,179 B2 | * | 10/2007 | Schneider | A47C 27/083 5/423 |
| 7,291,163 B2 | * | 11/2007 | Gammons | A61F 7/0097 607/104 |
| 7,507,249 B2 | | 3/2009 | Heaton et al. | |
| 7,727,267 B2 | * | 6/2010 | Lachenbruch | A61G 7/057 607/108 |
| 7,877,827 B2 | * | 2/2011 | Marquette | A47C 21/044 5/423 |
| 8,065,763 B2 | * | 11/2011 | Brykalski | A47C 21/048 5/423 |
| 8,181,290 B2 | * | 5/2012 | Brykalski | A47C 21/044 5/423 |
| 8,191,187 B2 | * | 6/2012 | Brykalski | A47C 21/044 5/423 |
| 8,800,078 B2 | | 8/2014 | Lachenbruch et al. | |
| 8,864,807 B2 | * | 10/2014 | Potter | A61F 7/0097 607/108 |
| 8,893,329 B2 | * | 11/2014 | Petrovski | A47C 21/044 5/421 |
| 9,222,685 B2 | * | 12/2015 | Lachenbruch | A47C 21/044 5/423 |
| 9,408,475 B2 | * | 8/2016 | Mikkelsen | A47G 9/1036 |
| 9,504,601 B1 | * | 11/2016 | Lewis | A61F 7/0085 |
| 9,717,638 B2 | * | 8/2017 | O'Reagan | A61G 7/057 |
| 2001/0020303 A1 | * | 9/2001 | Endo | A61F 7/00 5/421 |
| 2005/0262639 A1 | | 12/2005 | Butler | |
| 2006/0052851 A1 | * | 3/2006 | Anderson | A61F 7/0097 607/104 |
| 2008/0148481 A1 | * | 6/2008 | Brykalski | A47C 21/048 5/423 |
| 2009/0312823 A1 | * | 12/2009 | Patience | A61F 7/007 607/104 |
| 2013/0074272 A1 | | 3/2013 | Lachenbruch et al. | |
| 2014/0109314 A1 | * | 4/2014 | Boersma | A47C 21/044 5/423 |
| 2014/0237719 A1 | | 8/2014 | Brykalski et al. | |
| 2015/0257541 A1 | | 9/2015 | Lazakis | |
| 2015/0272338 A1 | * | 10/2015 | Greener | A47C 21/044 5/423 |

* cited by examiner

SUPPORT APPARATUSES COMPRISING COOLING ELEMENTS

CROSS-REFERENCE TO RELATED APPLICATION(S)

This application claims priority to U.S. Provisional Patent Application No. 62/439,933, filed on Dec. 29, 2016, the entire contents of which are herein incorporated by reference.

TECHNICAL FIELD

The present specification generally relates to support apparatuses, and more specifically, to support apparatuses comprising cooling elements.

BACKGROUND

Conventionally, a person confined to a hospital bed for an extended time may develop pressure ulcers. For example, when a person is in a supine position on the support surface, portions of the person's posterior skin, such as the person's sacral area, shoulder blades, and heels, may be subject to relatively high, localized pressure due to the person's own body weight. The areas of relatively high localized pressure may be prone to the development of pressure ulcers due to the localized increased pressure. The development of pressure ulcers may be further exacerbated by the presence of moisture, such as perspiration, trapped between the skin and the support surface for extended periods of time.

Accordingly, a need exists for patient support apparatuses that mitigate the development of pressure ulcers in persons positioned on the support apparatus.

SUMMARY

According to some embodiments of the present disclosure, a support apparatus configured to support a person is provided. The support apparatus includes a top surface including one or more predetermined areas, one or more conduits located inside the support apparatus which are located proximate to the one or more predetermined areas, and an air supply configured to provide air to the one or more conduits for delivering to the one or more predetermined areas. The air supply includes a temperature sensor configured to measure a temperature of the air provided by the air supply, a cooling element, and a controller communicatively coupled to the temperature sensor and the cooling element. The controller determines whether the measured temperature of the air is higher than a predetermined temperature, and controls the cooling element to cool the air to the predetermined temperature if it is determined that the temperature of the air is higher than the predetermined temperature.

According to some embodiments of the present disclosure, a support apparatus for supporting a person is provided. The support apparatus includes a top surface including one or more predetermined areas, one or more conduits located inside the support apparatus, a portion of one or more conduits being located proximate to the one or more predetermined areas, an air supply configured to provide air to the one or more conduits for delivering to the one or more predetermined areas, the air supply comprising a cooling element configured to cool the air to a predetermined temperature, and a self-powered generator supplying power to the air supply, the self-powered generator being located within the support apparatus.

Additional features and advantages will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

Referring now to the illustrative examples in the drawings, wherein like numerals represent the same or similar elements throughout.

DETAILED DESCRIPTION

Figure 1:
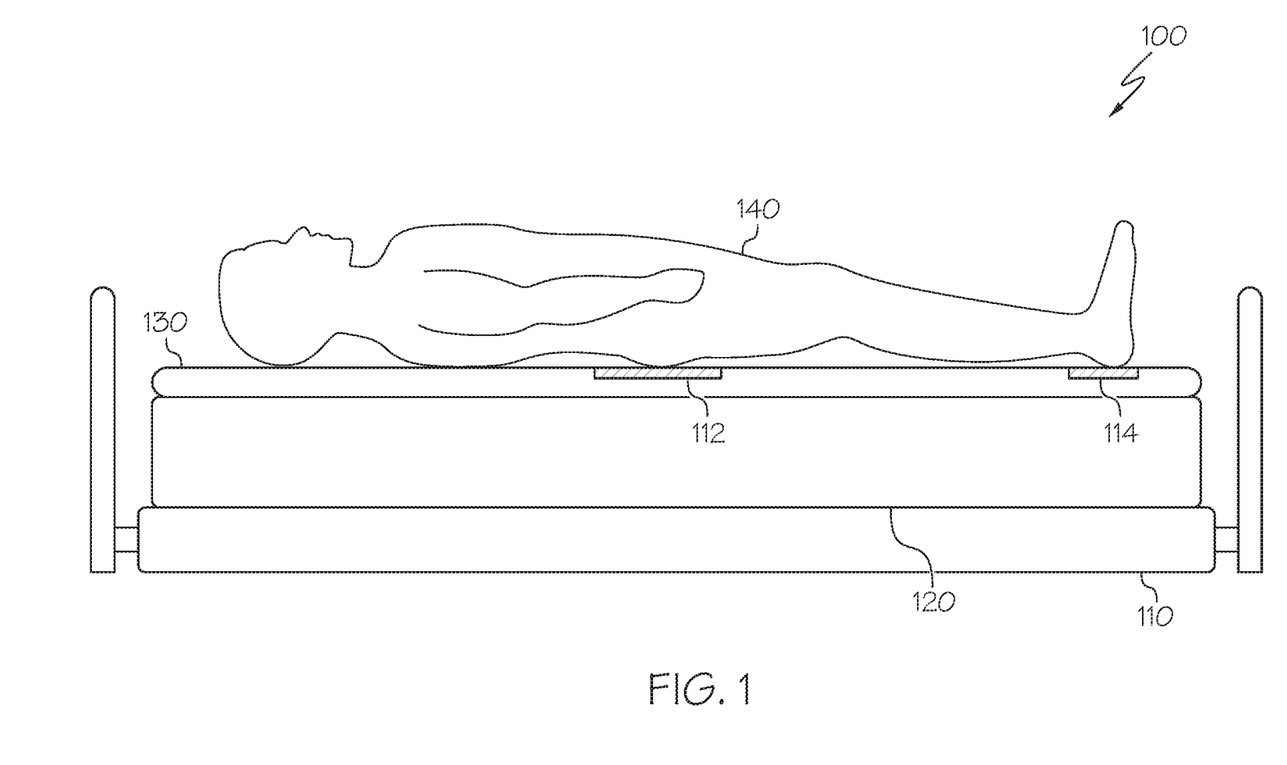
FIG. 1 depicts a side view of a person support system in accordance with one or more embodiments shown and described herein.

FIG. 1 generally depicts one embodiment of a person support system including a support apparatus having focal cooling features. As will be described, the person support system includes a mattress, and a support apparatus placed on the mattress. The support apparatus includes a top surface including one or more predetermined areas, one or more conduits located inside the support apparatus, an air supply configured to provide air to the one or more conduits, and a self-powered generator supplying power to the air supply. The air supply includes a temperature sensor configured to measure a temperature of the air, a cooling element for cooling the air, and a controller that determines whether the measured temperature of the air is higher than a predetermined temperature, and instructs the cooling element to cool the air to the predetermined temperature if it is determined that the temperature of the air is higher than the predetermined temperature. Various embodiments described herein include MCM cooling features of providing cooled air to certain areas on a support apparatus. The cooling features may reduce a temperature of the tissue in contact with the support apparatus, which may further reduce the likelihood of a pressure ulcer. Because the air supply which provides cooled air to certain areas on a support apparatus is embedded within the support apparatus and is powered by a power generator which is also integrated with the support apparatus, the present disclosure provides a simplified support apparatus which not only prevents pressure ulcers but also operates without external power source. In addition, the support apparatus may be easily transported because it is stiffened by pressure inside the support apparatus. Various embodiments of the support apparatus will be described in more detail herein.

Referring to FIG. 1, a person support system 100 is depicted. The person support system 100 may be, for example and without limitation, a hospital bed system. The person support system 100 generally includes a base frame 110, a mattress 120 that is supported by the base frame 110, and a support apparatus 130 that is placed on the mattress 120. The support apparatus 130 may have microclimate management (MCM) capability. Microclimate management (MCM) systems are typically used to cool and dry a patient's skin around the interface of the patient's skin with a support apparatus. Cool and dry skin is helpful to patient health and is less likely to develop decubitus ulcers during stays on the patient support system.

The support apparatus 130 may be filled with air, gel, three-dimensional engineered material or other suitable support material, or a combination of such materials. The support apparatus 130 may have a thickness of a half inch to three inches. For example, the support apparatus 130 may have a thickness of about one inch. A portion of the support apparatus 130 may be vapor permeable. For example, portions upon which a person 140 rests may be vapor permeable.

When the person 140 lies down on the support apparatus 130, the temperature of two physical areas 112 and 114 on the support apparatus 130 may be higher than other physical areas due to contact by the person 140. The physical area 112 may be an area on which a sacral area of the person 140 rests, and the physical area 114 may be an area on which a heel area of the person 140 rests. The support apparatus 130 includes a function of focal cooling the physical areas 112 and 114 through an air supply integrated inside the support apparatus 130, as will be described in detail below. The structure of the support apparatus will be described in greater detail below with reference to FIG. 2A.

Figure 2A:
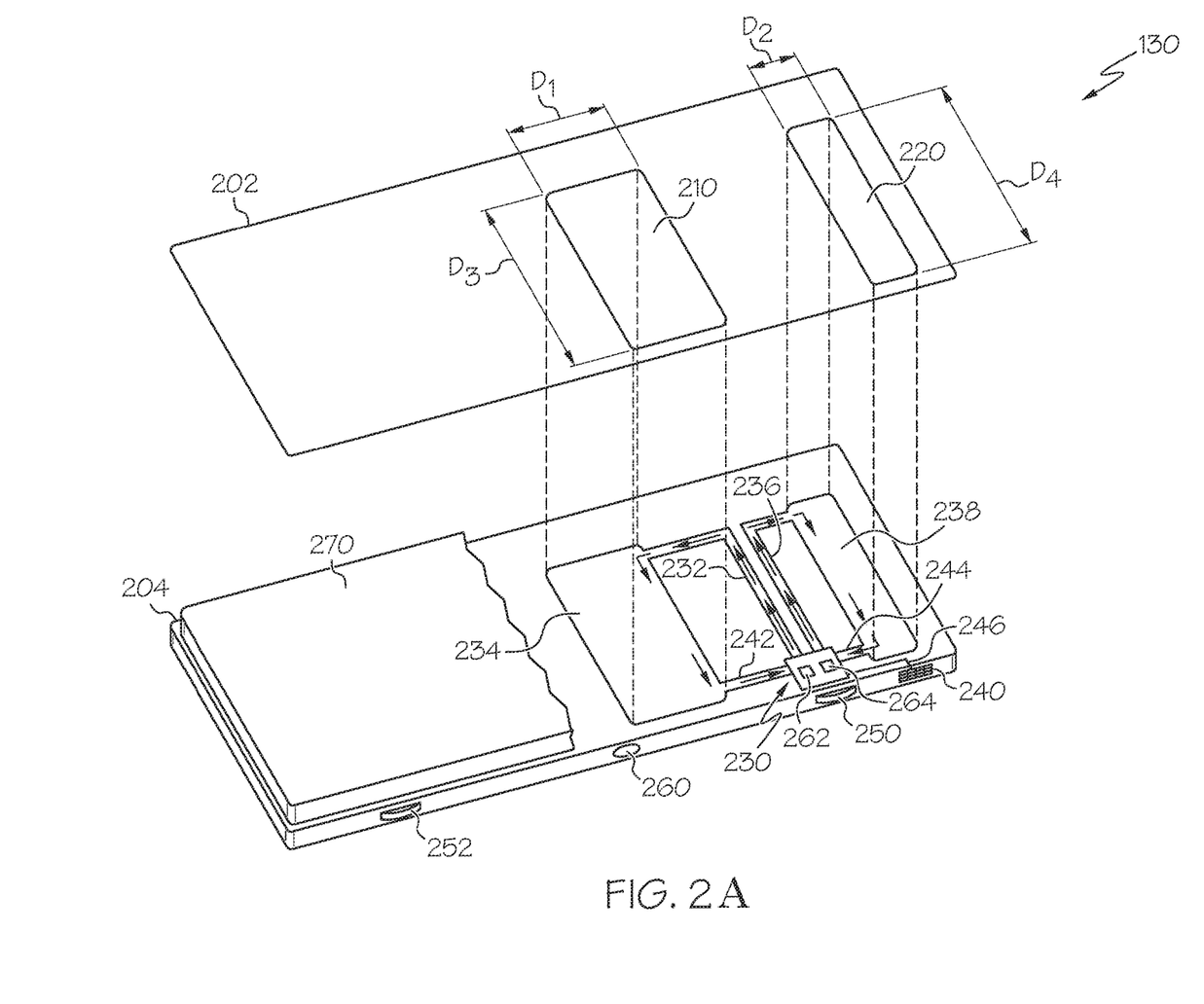
FIG. 2A depicts an exploded view of a support apparatus in accordance with one or more embodiments shown and described herein.

FIG. 2A is an exploded, schematic perspective view showing the support apparatus 130. The support apparatus 130 may include a top cover 202 and a bottom cover 204. The top cover 202 may include a plurality of microclimate management (MCM) zones. In some embodiments, the top cover 202 includes a first MCM zone 210 and a second MCM zone 220 which may correspond to the physical areas 112 and 114 of FIG. 1 respectively. The first MCM zone 210 and the second MCM zone 220 may be any shape, such as a square, a rectangle, an ellipse, a circle, etc., but not limited thereto. Although FIG. 2A illustrates first MCM zone 210 and the second MCM zone 220, the support apparatus 130 may include more than two MCM zones, or only one MCM zone in some embodiments. For example, the support apparatus 130 may include a third MCM zone on which a head of the person 140 rests in addition to the first MCM zone 210 and the second MCM zone 220.

The first MCM zone 210 may correspond to a physical area of concern related to a sacral area of the person 140 lying on the support apparatus 130. The first MCM zone 210 may have a length of D1 and a width of D3. The length D1 and the width D3 of the first MCM zone 210 may be determined based on statistical information on the lying position of people on the support apparatus 130. For example, the center of the first MCM zone 210 may be determined based on the center of an average sacral area of people lying on the support apparatus 130. The length D1 may be determined based on the variation of sacral areas of people contacting the support apparatus 130. The width D3 may be determined based on average lateral deviation of people lying on the support apparatus 130. In one embodiment, the length of D1 may be up to one third of the overall length of the support apparatus 130. For example, the length of D1 may be about 10 inches. The width of D3 may be up to the entire width of the support apparatus 130. For example, the width of D3 may be about 18 inches.

The second MCM zone 220 may correspond to a physical area of concern related to a heel area of a person lying on the support apparatus. The second MCM zone 220 may have a length of D2 and a width of D4. Similar to the first MCM zone 210, the length D2 and the width D4 of the second MCM zone 220 may be determined based on statistical information on the lying position of people on the support apparatus 130. For example, the center of the second MCM zone 220 may be determined based on the center of an average heel area of people lying on the support apparatus 130. The length D2 may be determined based on the variation of heel areas of people contacting the support apparatus 130. The width may be determined based on average lateral movement of feet of people lying on the support apparatus 130. In one embodiment, the length D2 may be up to one third of the total length of the support apparatus 130. For example, the length D2 may be about 20 inches. The width D4 may be the substantially same as the width of the support apparatus 130.

In one embodiment, both the first and second MCM zones may be indicated in a different color other than the rest of the area on the top cover 202 such that a caregiver can place sacral and heel portions of the person 140 inside the first MCM zone 210 and the second MCM zone 220 respectively. For example, the first MCM zone 210 and the second MCM zone 220 may be filled with a yellow color whereas the rest of the top cover 202 may be filled with a blue color. In other embodiments, the boundaries of the first MCM zone 210 and the second MCM zone 220 may be indicated on the top cover 202 to have a caregiver or a person know focal cooling zones. For example, the boundaries of the first MCM zone 210 and the second MCM zone 220 may be indicated with a dotted red line.

Inside the top cover 202 and the bottom cover 204 of the support apparatus 130, the support apparatus 130 includes an air supply 230, air conduits 232, 236, 242, and 244, air pockets 234 and 238, and cushioning material 270. In some embodiments, air may be provided into the support apparatus 130 through an air inlet 260 which will be described in detail below. For example, an external air pump may be attached to the air inlet 260 and provide air into the support apparatus 130. The air provided into the support apparatus 130 may provide sufficient pressure to stiffen the support apparatus 130 such that the support apparatus 130 would be deformed less by a force applied in a direction orthogonal to the support apparatus 130 than when the support apparatus 130 is not stiffened.

The air supply 230 may be connected with the air conduits 232, 236, 242, and 244. The air conduits 232, 236, 242 and 244 may be made of flexible plastic tubing, such as polyurethane tubing, or coated fabric, such as coated nylon. The air supply 230 may include a reservoir for retaining air from the air conduit 242 and the air conduit 244. Some embodiments may not include a reservoir, such as embodiments that cool circulated air. The air supply 230 may be electrically coupled to a power generator 240 and powered by the power generator 240. The air supply 230 may circulate air through the air conduits 232, 236, 242, and 244. Specifically, the air supply 230 may receive air from the air conduit 242 and provide the air to the air conduit 232 such that the air circulates in a direction as indicated by arrows in FIG. 2A. Similarly, the air supply 230 may receive air from the air conduit 244 and provide the air to the air conduit 236 such that the air circulates in a direction as indicated by arrows in FIG. 2A.

The air supply 230 may include a cooling element 262 and a temperature sensor 264. The cooling element 262 may be a thermoelectric cooling device. In other embodiments, the cooling element 262 may be an active cooling apparatus such as a chiller or may be a passive cooling apparatus such as a nozzle. The cooling element 262 cools the air to a certain temperature, e.g., 75 Fahrenheit degree. The cooled air may be provided to the air pockets 234 and 238 through the air conduits 232 and 236 respectively. The air pockets 234 and 238 may maintain air pressure therein. The shape of air pockets 234 and 238 may correspond to the first and second MCM zones 210 and 220 respectively. In this regard, the cooled air in the air pockets 234 and 238 cools the first and second MCM zones 210 and 220.

The temperature sensor 264 may measure the temperature of the air within the air supply 230. If the temperature sensor 264 detects that the temperature of the air is over 75 Fahrenheit degree, the air supply 230 cools the air in its reservoir (or the circulating air in embodiments that do not include the reservoir) to 75 Fahrenheit degree using the cooling element 262, and provides the cooled air to the air pockets 234 and 238. In another embodiment, two temperature sensors may be located proximate to the air pocket 234 and the air pocket 238 respectively, and measure the temperature of air within the air pocket 234 and the air pocket 238. The temperature sensors may be communicatively coupled to the air supply 230, and may provide the measured temperature to the air supply 230. Based on the measured temperature, the air supply 230 may cool air within its storage and circulate the cooled air. The cooled air may be provided to the air pocket 234 and the air pocket 238 via the air conduits 232 and 236 respectively, and the temperature of the air within the air pockets 234 and 238 is lowered to a certain temperature, e.g., 75 Fahrenheit degree.

The cushioning material 270 may be porous foam. The porous foam made from a light density foam to facilitate easy air flow through the support apparatus 130. For example, air supplied through an air inlet 260 may easily flow inside the support apparatus 130. The air pockets 234 and 238 may be deposited on the cushioning material 270 such that the air pockets 234 and 238 can effectively cool the first and second MCM zones 210 and 220.

The surface of the bottom cover 204 includes a power generator 240, pull straps 250 and 252, and an air inlet 260.

The power generator 240 may be photoelectric cells. The photoelectric cells generate power when they receive ambient lights. The power generator 240 supplies power to the air supply 230 through a connection 246 such as a conductive wire. In other embodiments, the power generator 240 may include an opening for receiving a chargeable or rechargeable battery which supplies power to the power generator 240. One or more power generators 240 may be attached on the bottom cover 204. The number of power generators 240 may be determined based on the power consumption by the air supply 230. In another embodiment, the power generator 240 may include a rechargeable battery, and the surface of the bottom cover 204 may include a power port for receiving external power (e.g., from external power cord plugged into the wall). The rechargeable battery may be charged while the support apparatus receives power from an external power source through the power port.

The pull straps 250 and 252 may be located on the side of the support apparatus 130 as shown in FIG. 2A. The pull straps 250 and 252 allow an operator to easily move the support apparatus 130 from one platform to another even when a person is on the support apparatus 130. Because the support apparatus 130 is stiffened by air pressure due to air retained inside the support apparatus 130 and may not be deformed by a force applied in a direction orthogonal to the support apparatus 130, a less force is required to move the support apparatus 130 from one platform to another using the pull straps 250 and 252 when the support apparatus 130 is stiffened.

Figure 2B:
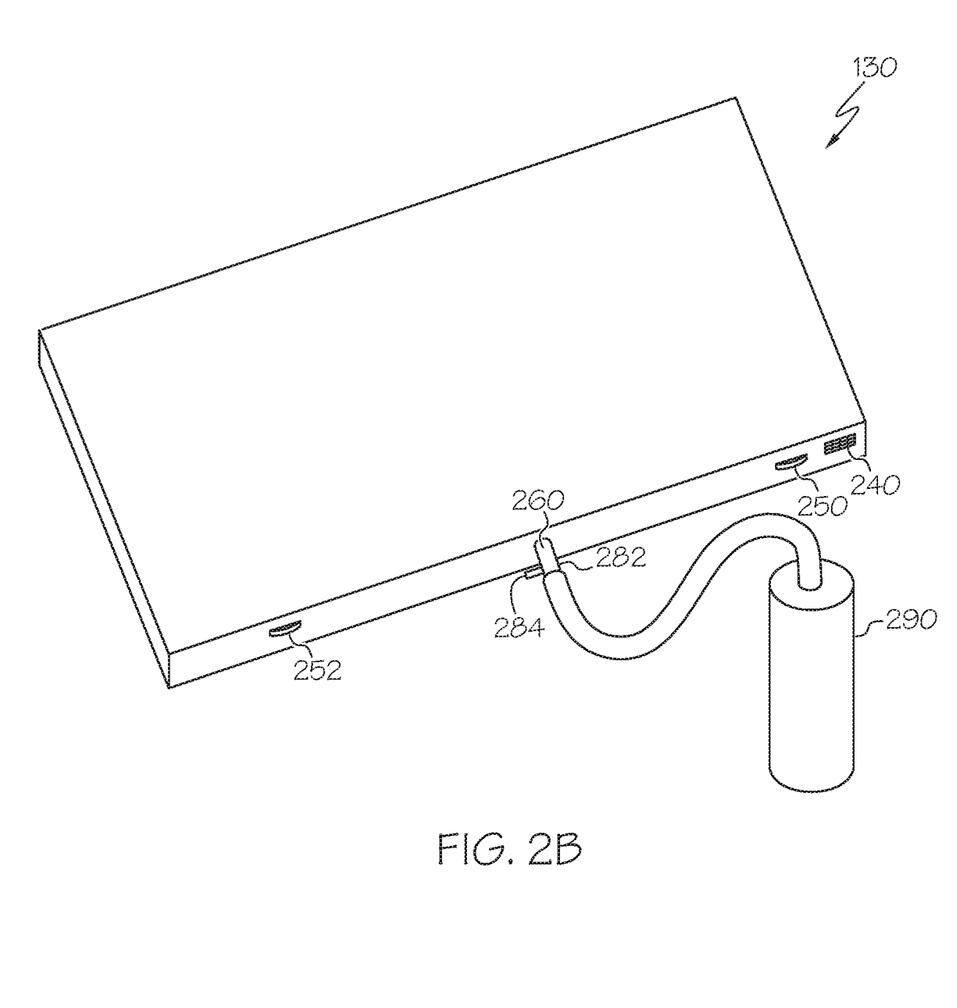
FIG. 2B depicts a support apparatus receiving compressed air from an external compressor in accordance with one or more embodiments shown and described herein.

The air inlet 260 allows air to be supplied into the support apparatus 130 such that air pressure inside the support apparatus 130 is maintained at a certain level. The air inlet 260 may be securely sealed after air is supplied into the support apparatus 130. In FIG. 2B, the air inlet 260 may include a one-way check valve 282 with a relief device 284. The relief device 284 may allow the support apparatus 130 to deflate when desired. In another embodiment, the air inlet 260 may include a valve which allows air to flow into the support apparatus 130 or flow out from the support apparatus 130. In some embodiments, the air inlet 260 may include a valve that may be pinched such that air may be introduced into the support apparatus 130 via the air inlet 260 or be released from the support apparatus 130 via the air inlet 260 when the valve is in a pinched configuration and that air may be retained within the support apparatus 130 when the valve is in an unpinched configuration. The support apparatus 130 may be filled with compressed air. For example, an external compressor 290 may supply compressed air into the support apparatus 130 via the air inlet 260 to stiffen the support apparatus 130 such that the support apparatus 130 would be deformed less by a force applied in a direction orthogonal to the support apparatus 130 than when the support apparatus 130 is not stiffened.

Figure 3:
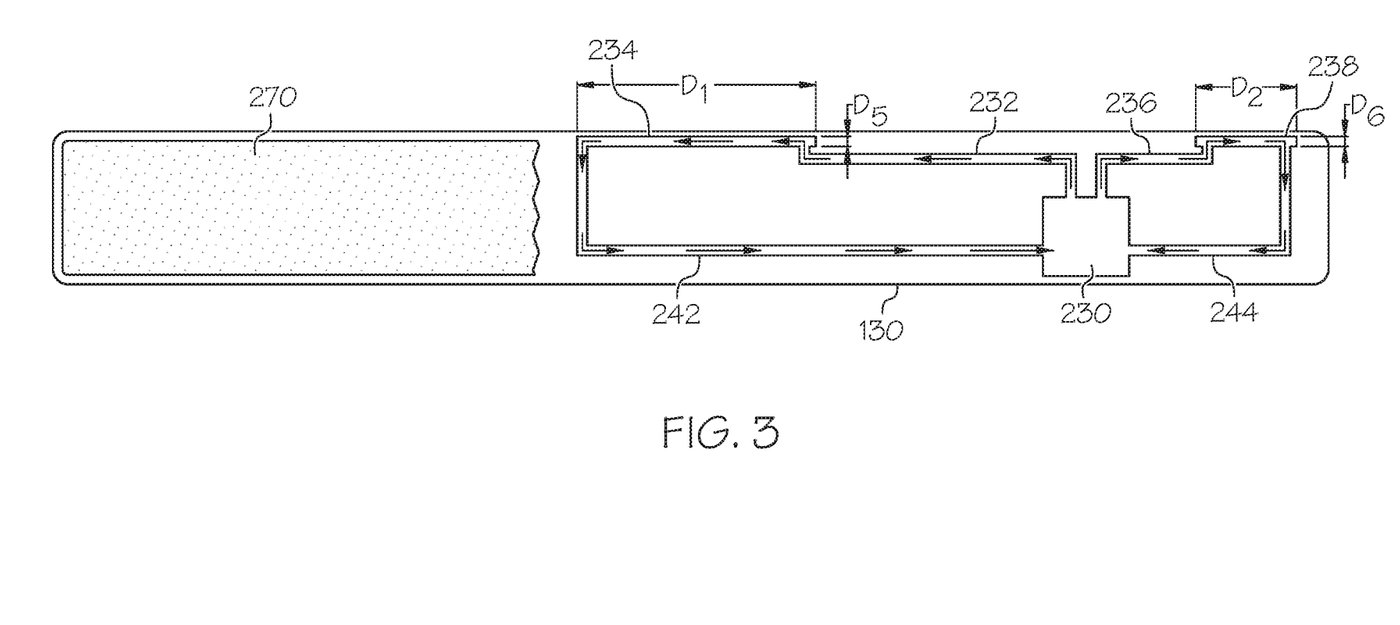
FIG. 3 depicts a sectional view of a support apparatus in accordance with one or more embodiments shown and described herein.

FIG. 3 is a sectional view of the support apparatus. The support apparatus 130 includes the air supply 230, the air conduits 232, 236, 242, and 244, the air pockets 234 and 238, and the cushioning material 270. As described with reference to FIG. 2A above, the air supply 230 circulates air via the air conduit 232, the air pocket 234 and the air conduit 242. The air supply 230 may cool the air to a certain temperature using the cooling element 262, and blow the cooled air to the air pockets 234 and 238 respectively. The air pocket 234 may have a height of D5 and the air pocket 238 may have a height of D6. The height D5 may be between a quarter inch to three inches. For example, the height D5 may be about one inch. The height D6 may be between a quarter inch to three inches. For example, the height D6 may be about one inch.

Figure 4:
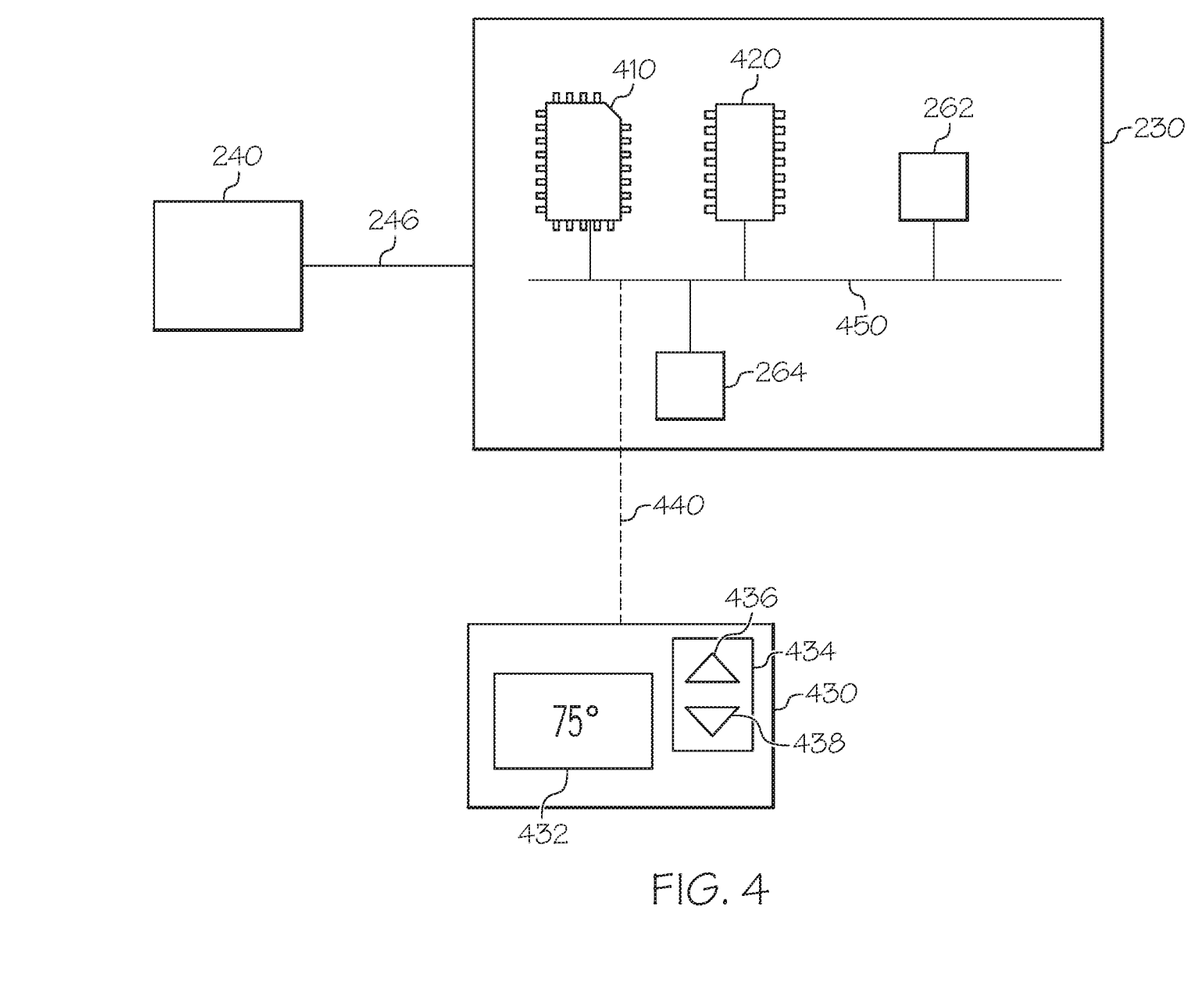
FIG. 4 schematically depicts the air supply of the support apparatus in accordance with one or more embodiments shown and described herein.

FIG. 4 schematically depicts the air supply of the support apparatus according to one or more embodiments shown and described herein. The air supply 230 may include one or more processors 410. Each of the one or more processors 410 may be any device capable of executing machine readable instructions. For example, each of the one or more processors 410 may be a controller, an integrated circuit, a microchip, a computer, or any other computing device. The one or more processors 410 are coupled to a communication path 450 that provides signal interconnectivity between various modules of the air supply. Accordingly, the communication path 450 may communicatively couple any number of processors 410 with one another, and allow the modules coupled to the communication path 450 to operate in a distributed computing environment. Specifically, each of the modules may operate as a node that may send and/or receive data. As used herein, the term "communicatively coupled" means that coupled components are capable of exchanging data signals with one another such as, for example, electrical signals via conductive medium, electromagnetic signals via air, optical signals via optical waveguides, and the like.

Accordingly, it should be understood that the communication path 450 may be formed from any medium that is capable of transmitting a signal such as, for example, conductive wires, conductive traces, optical waveguides, or the like. In some embodiments, the communication path 450 may facilitate the transmission of wireless signals, such as WiFi, Bluetooth, Near Field Communication (NFC) and the like. Moreover, the communication path 450 may be formed from a combination of mediums capable of transmitting signals. In one embodiment, the communication path 450 comprises a combination of conductive traces, conductive wires, connectors, and buses that cooperate to permit the transmission of electrical data signals to components such as processors, memories, sensors, input devices, output devices, and communication devices. In embodiments, the communication path 450 may comprise a vehicle bus, such as for example a LIN bus, a CAN bus, a VAN bus, and the like. Additionally, it is noted that the term "signal" means a waveform (e.g., electrical, optical, magnetic, mechanical or electromagnetic), such as DC, AC, sinusoidal-wave, triangular-wave, square-wave, vibration, and the like, capable of traveling through a medium.

The air supply 230 may further include one or more memory modules 420 coupled to the communication path 450. The one or more memory modules 420 may comprise RAM, ROM, flash memories, hard drives, or any device capable of storing machine readable instructions such that the machine readable instructions can be accessed by the one or more processors 410. The one or more memory modules 420 may be non-transient memory modules. The machine readable instructions may comprise logic or algorithm(s) written in any programming language of any generation (e.g., 1GL, 2GL, 3GL, 4GL, or 5GL) such as, for example, machine language that may be directly executed by the processor, or assembly language, object-oriented programming (OOP), scripting languages, microcode, etc., that may be compiled or assembled into machine readable instructions and stored on the one or more memory modules 420. Alternatively, the machine readable instructions may be written in a hardware description language (HDL), such as logic implemented via either a field-programmable gate array (FPGA) configuration or an application-specific integrated circuit (ASIC), or their equivalents. Accordingly, the methods described herein may be implemented in any conventional computer programming language, as pre-programmed hardware elements, or as a combination of hardware and software components.

In some embodiments, the one or more memory modules 420 may store information on a threshold temperature set by a user. For example, the one or more memory modules 420 may store a temperature of 75 Fahrenheit as a threshold temperature. The one or more memory modules 420 may store a history of temperatures detected by the temperature sensor 264.

The air supply 230 includes the cooling element 262 described above with reference to FIG. 2A. The cooling element 262 is coupled to the communication path 450 such that the communication path 450 communicatively couples the cooling element 262 to other modules of the air supply 230.

The air supply 230 includes the temperature sensor 264 described above with reference to FIG. 2A. The temperature sensor 264 is coupled to the communication path 450 such that the communication path 450 communicatively couples the temperature sensor 264 to other modules of the air supply 230. For example, the temperature sensor 264 may measure the temperature of the air within the air supply 230 and provide the measured temperature to the one or more processors 410 and/or the one or more memory modules 420. Then, the one or more processors 410 may determine whether the measured temperature is higher than a threshold temperature. If it is determined that the measured temperature is higher than the threshold temperature, the one or more processors 410 may instruct the cooling element 262 to cool the air.

The air supply 230 is communicatively coupled to a temperature setting module 430 via a communication path 440. The temperature setting module 430 may be located on the surface of the support apparatus 130. In other embodiment, the temperature setting module 430 may be a separate device from the support apparatus 130 and communicate with the air supply 230 of the support apparatus 130 wirelessly. The temperature setting module 430 may include a display 432 and a tactile input hardware 434.

The display 432 may display a temperature preset by a user. For example, the display 432 may receive a preset temperature from the one or more memory modules 420 and display the preset temperature. The display 432 may include any medium capable of transmitting an optical output such as, for example, a cathode ray tube, a light emitting diode (LED) display, an organic light emitting diode (OLED) display, a liquid crystal display, a plasma display, or the like. In embodiments, the display 432 may be a touchscreen that, in addition to visually displaying information, detects the presence and location of a tactile input upon a surface of or adjacent to the display 432. Accordingly, each display may receive mechanical (e.g., touch) input directly upon the optical output provided by the screen. Additionally, it is noted that the display 432 can include at least one of the one or more processors 410 and at least one of the one or memory modules 420.

The tactile input hardware 434 may be any device capable of transforming mechanical, optical, or electrical signals into a data signal. Specifically, the tactile input hardware 434 may include any number of movable objects that each transform physical motion into a data signal that can be transmitted over the communication path 440 such as, for example, a button, a switch, a knob, a microphone or the like. In one embodiment, the tactile input hardware 434 includes two arrow buttons for adjusting the preset temperature as shown in FIG. 4. For example, when the upper arrow button 436 is pressed once, the preset temperature may increase by the amount of one Fahrenheit degree, and the increased preset temperature may be displayed on the display 432. When the lower arrow button 438 is pressed once, the preset temperature may decrease by the amount of one Fahrenheit degree, and the decreased preset temperature may be displayed on the display 432. The adjusted preset temperature may be transmitted to the air supply 230 via the communication path 440.

The communication path 440 may be formed from any medium that is capable of transmitting a signal such as, for example, conductive wires, conductive traces, optical waveguides, or the like. In some embodiments, the communication path 440 may facilitate the transmission of wireless signals, such as WiFi, Bluetooth, Near Field Communication (NFC) and the like. Moreover, the communication path 440 may be formed from a combination of mediums capable of transmitting signals. In one embodiment, the communication path 440 comprises a combination of conductive traces, conductive wires, connectors, and buses that cooperate to permit the transmission of electrical data signals to components such as processors, memories, sensors, input devices, output devices, and communication devices. In embodiments, the communication path 440 may comprise a vehicle bus, such as for example a LIN bus, a CAN bus, a VAN bus, and the like. Additionally, it is noted that the term "signal" means a waveform (e.g., electrical, optical, magnetic, mechanical or electromagnetic), such as DC, AC, sinusoidal-wave, triangular-wave, square-wave, vibration, and the like, capable of traveling through a medium.

The air supply 230 may be connected with the power generator 240 through the connection 246. As discussed above, the power generator 240 may be photoelectric cells. The photoelectric cells generate power when they receive ambient lights. The power generator 240 supplies power to the air supply 230 through the connection 246 such as a conductive wire.

Figure 5:
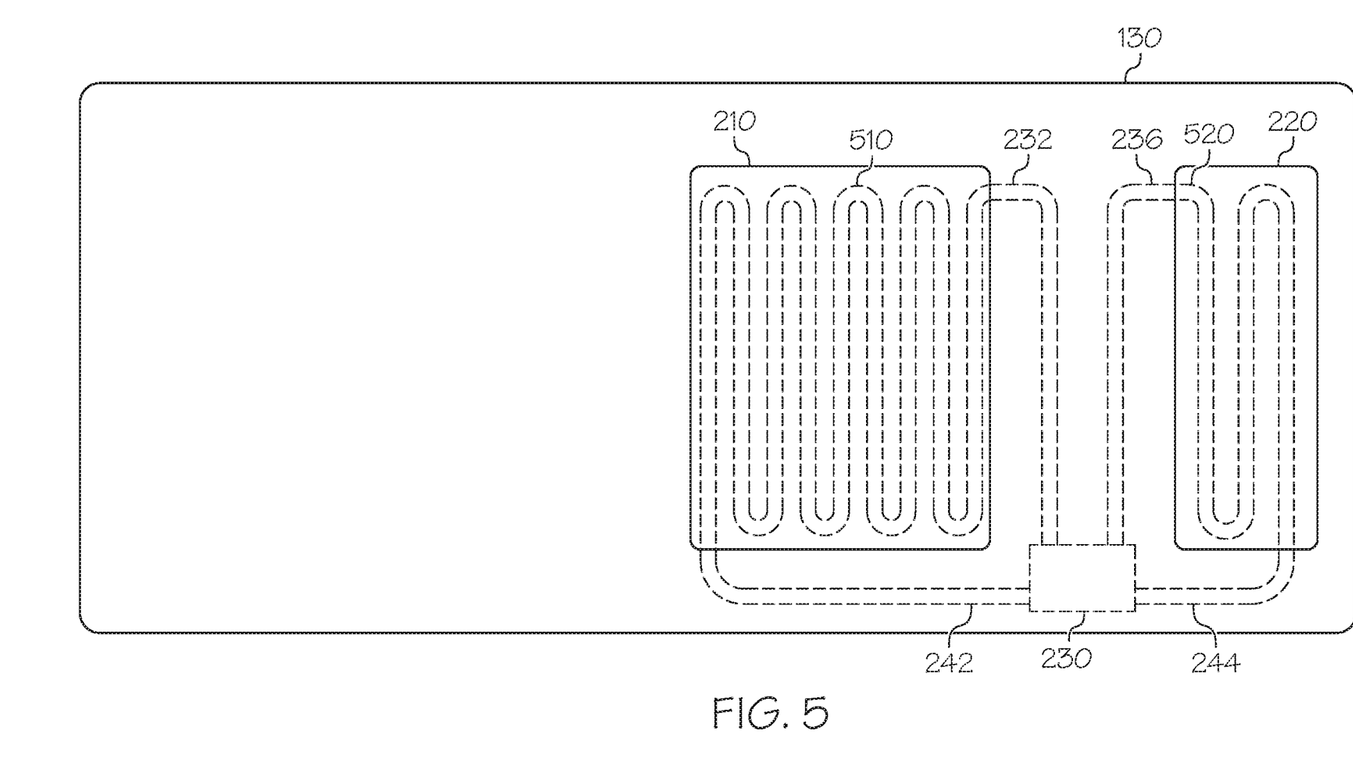
FIG. 5 depicts a top view of a support apparatus in accordance with one or more embodiments shown and described herein.

FIG. 5 is a top view of the support apparatus 130 having a different cooling structure in accordance with another embodiment shown and described herein. As shown in FIG. 5, the support apparatus 130 includes the air supply 230, the air conduits 232, 236, 242, and 244, and cooling conduits 510 and 520. The air supply 230 is connected with the air conduits 232 and 236. The air conduits 232 and 236 are connected with the cooling conduits 510 and 520, respectively, which are connected with the air conduits 242 and 244. Thus, the air provided by the air supply 230 may flow through the air conduit 232, the cooling conduit 510, and the air conduit 242. Similarly, the air provided by the air supply 230 may flow through the air conduit 236, the cooling conduit 520, and the air conduit 244. The air supply 230 may be powered by a power generator (not shown) positioned on the support apparatus 130.

In this embodiment, the support apparatus 130 uses the cooling conduits 510 and 520 instead of the air pockets described in reference to FIGS. 2-3. The cooling conduits 510 and 520 may be shaped in a repetitive wave form (e.g., a repetitive w shape) as shown in FIG. 5. The cooling conduits 510 and 520 in a repetitive wave shape can efficiently cool down the first and second MCM zones 210 and 220 because the air traveling the cooling conduits 510 or 520 may uniformly cool the first MCM zone 210 and the second MCM zone 220 as compared with the air traveling the air pocket 234 or 238 shown in FIG. 2A.

Figure 6:
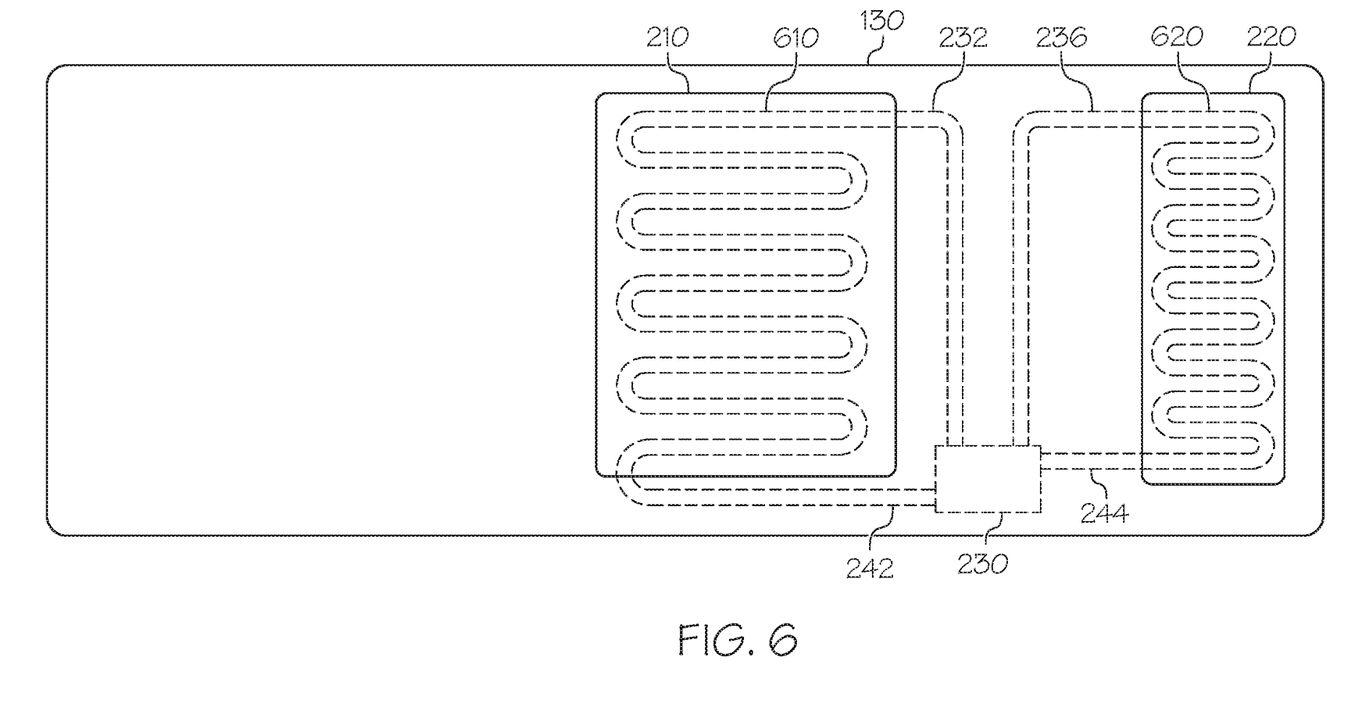
FIG. 6 depicts a top view of a support apparatus in accordance with one or more embodiments shown and described herein.

FIG. 6 is a top view of the support apparatus 130 having a different cooling structure in accordance with another embodiment shown and described herein. Similar to FIG. 5, the support apparatus 130 includes the air supply 230, the air conduits 232, 236, 242, and 244, and cooling conduits 610 and 620. The air supply 230 is connected with the air conduits 232 and 236. The air conduits 232 and 236 are connected with the cooling conduits 610 and 620, respectively, which are connected with the air conduits 242 and 244. Thus, the air provided by the air supply 230 may flow through the air conduit 232, the cooling conduit 610, and the air conduit 242. Similarly, the air provided by the air supply 230 may flow through the air conduit 236, the cooling conduit 620, and the air conduit 244. The air supply 230 may be powered by a power generator (not shown) positioned on the support apparatus 130. The cooling conduits 610 and 620 may be also shaped in a repetitive wave form as the cooling conduits 510 and 520, but have different pattern as shown in FIG. 6.

Figure 7A:
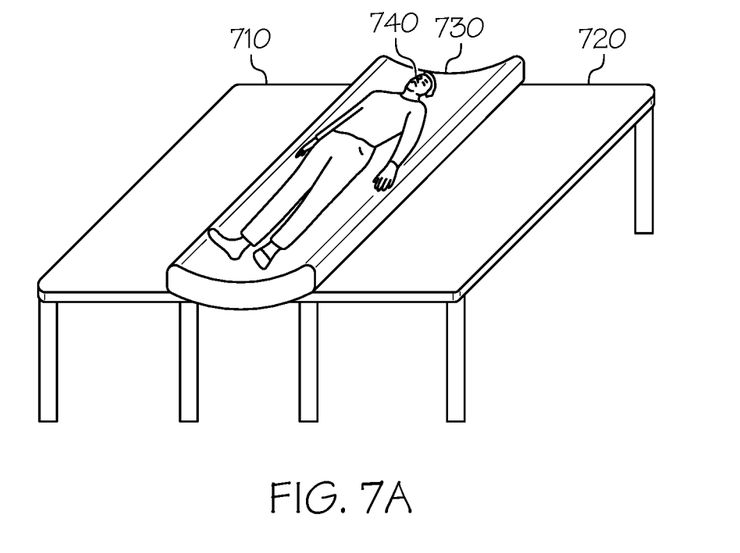
FIG. 7A schematically depicts moving a conventional support apparatus on which a patient rests from one platform to another platform in accordance with one or more embodiments shown and described herein.

FIG. 7A depicts moving a conventional support apparatus on which a patient rests from one platform to another platform. Because the conventional support apparatus 730 is usually made of flexible foam materials, the conventional support apparatus 730 is deformed (e.g., bended) when placed between a first platform 710 and a second platform 720 due to the weight of the patient 740 which applies a force in a direction orthogonal to the conventional support apparatus 730.

Figure 7B:
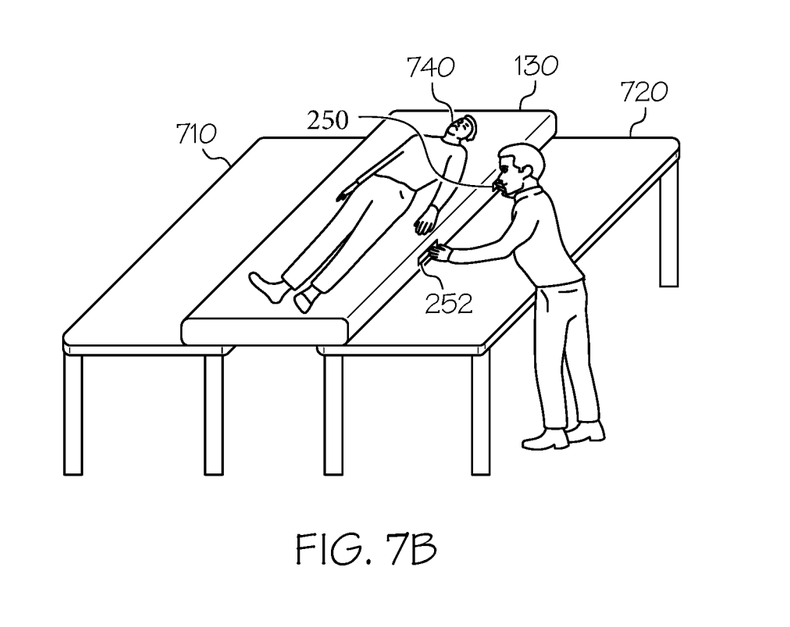
FIG. 7B schematically depicts moving a support apparatus from one platform to another platform in accordance with one or more embodiments shown and described herein.

FIG. 7B depicts moving a support apparatus from one platform to another platform in accordance with one or more embodiments shown and described herein. In FIG. 7B, the support apparatus 130 according to an embodiment of the present disclosure is rigid enough to endure the weight of the patient 740 and does not bend even when it is placed between the first platform 710 and the second platform 720. Because the support apparatus 130 does not bend, much less force is required to move the support apparatus 130 from the first platform 710 to the second platform 720. In addition, the pull straps 250 and 252 on the side of the support apparatus 130 facilitate the transfer of the support apparatus 130.

Various embodiments described herein include MCM cooling features of providing cooled air to certain areas on a support apparatus. The cooling features may reduce a temperature of the tissue in contact with the support apparatus, which may further reduce the likelihood of a pressure ulcer. Because the air supply which provides cooled air to certain areas on a support apparatus is embedded within the support apparatus and is powered by a power generator which is also integrated with the support apparatus, the present disclosure provides a simplified support apparatus which not only prevents pressure ulcers but also operates without external power source. In addition, the support apparatus may be easily transported because it is stiffened by pressure inside the support apparatus.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A support apparatus configured to be placed on a mattress and configured to support a person, the support apparatus comprising:

a top surface including a first predetermined area and a second predetermined area separated from the first predetermined area; and an enclosed area comprising:
- a first conduit and a second conduit located inside the enclosed area of the support apparatus, the first conduit connected to a first air pocket located proximate to the first predetermined area, the second conduit connected to a second air pocket located proximate to the second predetermined area; and
- an air supply positioned inside the enclosed area of the support apparatus and directly connected to the first conduit and the second conduit, the air supply configured to provide air to the first and second conduits simultaneously for delivering to the first and second predetermined areas, wherein one end of each of the first and second conduits and the other end of each of the first and second conduits are directly connected to the air supply, the air supply comprising:

a temperature sensor configured to measure a temperature of the air provided by the air supply;

a cooling element; and a controller communicatively coupled to the temperature sensor and the cooling element, the controller comprising at least one processor and at least one memory storing computer readable and executable instructions that, when executed by the processor, cause the controller to:

determine whether the measured temperature of the air is higher than a predetermined temperature; and control the cooling element to cool the air to the predetermined temperature if it is determined that the temperature of the air is higher than the predetermined temperature, wherein an entirety of the first air pocket is at a vertically higher position inside the enclosed area than an entirety of the first conduit, and an entirety of the second air pocket is at a vertically higher position than an entirety of the second conduit.

2. The support apparatus of claim 1, further comprising a self-powered generator supplying power to the air supply, the self-powered generator being located within the support apparatus.

3. The support apparatus of claim 2, wherein the self-powered generator comprises one or more photoelectric cells.

4. The support apparatus of claim 1, wherein the predetermined temperature is about 75° F.

5. The support apparatus of claim 1, wherein the support apparatus comprises a plurality of pull straps attached to lateral sides of the support apparatus.

6. The support apparatus of claim 1, wherein the first predetermined area comprises an area corresponding to a sacral area of the person when the person rests on the support apparatus.

7. The support apparatus of claim 1, wherein the second predetermined area comprises an area corresponding to a heel area of the person when the person rests on the support apparatus.

8. The support apparatus of claim 1, further comprising an air inlet for receiving compressed air from outside the support apparatus.

9. The support apparatus of claim 8, wherein the air inlet comprises:
- a check valve coupled to the air inlet and configured to receive the compressed air from an external compressor; and
- a relief device configured to expel the compressed air within the support apparatus.

10. The support apparatus of claim 8, wherein the support apparatus is configured to be filled with the compressed air such that the support apparatus is deformed less by a force applied in a direction orthogonal to the support apparatus than when the support apparatus is not filled with the compressed air.

11. The support apparatus of claim 1, wherein the temperature sensor is located proximate to the one or more predetermined areas.

12. The support apparatus of claim 1, further comprising a temperature setting module, communicatively coupled to the air supply, the temperature setting module comprising:
- a display; and
- a tactile input hardware configured to receive input indication of a request to adjust the predetermined temperature.

13. The support apparatus of claim 1, wherein the first and second predetermined areas of the top surface have a color different from a rest of the top surface.

14. The support apparatus of claim 1, wherein boundaries of the first and second predetermined areas of the top surface are indicated on the top surface.

15. A person support system comprising:
- a mattress; and
- the support apparatus of claim 1 coupled to the mattress.

16. A support apparatus configured to be placed on a mattress and configured to support a person, the support apparatus comprising:

a top surface including a first predetermined area and a second predetermined area separated from the first predetermined area; and an enclosed area comprising:
- a first conduit and a second conduit located inside the enclosed area of the support apparatus, the first conduit connected to a first cooling conduit located proximate to the first predetermined area, the second conduit connected to a second cooling conduit located proximate to the second predetermined area; and
- an air supply positioned inside the enclosed area of the support apparatus and directly connected to the first conduit and the second conduit, the air supply configured to provide air to the first and second conduits simultaneously for delivering to the first and second predetermined areas, wherein one end of each of the first and second conduits and the other end of each of the first and second conduits are directly connected to the air supply, the air supply comprising:

a temperature sensor configured to measure a temperature of the air provided by the air supply;

a cooling element; and a controller communicatively coupled to the temperature sensor and the cooling element, the controller comprising at least one processor and at least one memory storing computer readable and executable instructions that, when executed by the processor, cause the controller to:

determine whether the measured temperature of the air is higher than a predetermined temperature; and control the cooling element to cool the air to the predetermined temperature if it is determined that the temperature of the air is higher than the predetermined temperature, wherein an entirety of the first cooling conduit is at a vertically higher position inside the enclosed area than an entirety of the first conduit, and an entirety of the second cooling conduit is at a vertically higher position than an entirety of the second conduit.

17. A support apparatus for supporting a person, the support apparatus comprising:
a top surface including a first predetermined area and a second predetermined area separated from the first predetermined area; and an enclosed area comprising:
first and second conduits located inside the enclosed area of the support apparatus, the first conduit including a first air pocket located proximate to the first predetermined area, the second conduit including a second air pocket located proximate to the second predetermined area;
an air supply positioned inside the enclosed area of the support apparatus and directly connected to the first conduit and the second conduit, the air supply configured to provide air to the first and second conduits simultaneously for delivering to the first and second predetermined areas, the air supply comprising a cooling element configured to cool the air to a predetermined temperature, wherein one end of each of the first and second conduits and the other end of each of the first and second conduits are directly connected to the air supply; and
a self-powered generator supplying power to the air supply, the self-powered generator being located within the support apparatus,
wherein an entirety of the first air pocket is at a vertically higher position inside the enclosed area than an entirety of the first conduit, and an entirety of the second air pocket is at a vertically higher position than an entirety of the second conduit.

18. The support apparatus of claim 17, further comprising a temperature sensor configured to measure a temperature of the air.

* * * * *